United States Patent
Claus et al.

(10) Patent No.: US 7,950,849 B2
(45) Date of Patent: May 31, 2011

(54) METHOD AND DEVICE FOR GEOMETRY ANALYSIS AND CALIBRATION OF VOLUMETRIC IMAGING SYSTEMS

(75) Inventors: Bernhard Erich Hermann Claus, Niskayuna, NY (US); Joseph John Manak, Albany, NY (US)

(73) Assignee: General Electric Company, Niskayuna, NY (US)

( * ) Notice: Subject to any disclaimer, the term of this patent is extended or adjusted under 35 U.S.C. 154(b) by 1435 days.

(21) Appl. No.: 11/289,346

(22) Filed: Nov. 29, 2005

(65) Prior Publication Data

US 2007/0122020 A1     May 31, 2007

(51) Int. Cl.
    *G01D 18/00*     (2006.01)
(52) U.S. Cl. .......................................... 378/207; 378/18
(58) Field of Classification Search ............... 378/18, 378/207
See application file for complete search history.

(56) References Cited

U.S. PATENT DOCUMENTS

| | | | |
|---|---|---|---|
| 5,214,578 A * | 5/1993 | Cornuejols et al. | 378/207 |
| 5,442,674 A | 8/1995 | Picard et al. | |
| 6,206,566 B1 * | 3/2001 | Schuetz | 378/205 |
| 6,379,043 B1 * | 4/2002 | Zylka et al. | 378/207 |
| 6,382,835 B2 * | 5/2002 | Graumann et al. | 378/198 |
| 6,466,638 B1 * | 10/2002 | Silver et al. | 378/4 |
| 6,491,430 B1 * | 12/2002 | Seissler | 378/207 |
| 7,269,243 B2 * | 9/2007 | Chell et al. | 378/18 |
| 7,494,278 B2 * | 2/2009 | Ritter | 378/207 |
| 2002/0041655 A1 * | 4/2002 | Mitschke | 378/207 |
| 2005/0094771 A1 * | 5/2005 | Basu et al. | 378/207 |

\* cited by examiner

*Primary Examiner* — Edward J Glick
*Assistant Examiner* — Alexander H Taningco
(74) *Attorney, Agent, or Firm* — Jason K. Klindtworth

(57) ABSTRACT

A technique is provided for geometrical analysis and calibration of a volumetric imaging system. The technique includes computing a projection error between estimated locations of a set of markers of a phantom based on a estimated imaging geometry and observed locations of the respective markers for at least one projection image, decomposing the computed projection error into one or more error components corresponding to respective geometric parameters of the imaging geometry, and updating at least one parameter of the estimated imaging geometry based on the one or more error components.

22 Claims, 7 Drawing Sheets

$$\begin{pmatrix} 0 & 1 & -1 & 1 & 1 & 0 & 1 & -1 & 0 \\ 1 & 0 & -1 & -1 & 0 & 1 & 1 & 0 & -1 \\ 0 & 1 & 1 & 1 & 1 & 0 & -1 & 1 & 0 \\ 1 & 0 & -1 & 1 & 0 & 1 & 1 & 0 & 1 \\ 0 & 1 & 1 & -1 & 1 & 0 & -1 & -1 & 0 \\ 1 & 0 & 1 & 1 & 0 & 1 & -1 & 0 & -1 \\ 0 & 1 & -1 & -1 & 1 & 0 & 1 & 1 & 0 \\ 1 & 0 & 1 & -1 & 0 & 1 & -1 & 0 & 1 \\ 0 & 1 & -1 & 1 & -1 & 0 & -1 & -1 & 0 \\ 1 & 0 & -1 & -1 & 0 & -1 & -1 & 0 & -1 \\ 0 & 1 & 1 & 1 & -1 & 0 & 1 & 1 & 0 \\ 1 & 0 & -1 & 1 & 0 & -1 & -1 & 0 & 1 \\ 0 & 1 & 1 & -1 & -1 & 0 & 1 & -1 & 0 \\ 1 & 0 & 1 & 1 & 0 & -1 & 1 & 0 & -1 \\ 0 & 1 & -1 & -1 & -1 & 0 & -1 & 1 & 0 \\ 1 & 0 & 1 & -1 & 0 & -1 & 1 & 0 & 1 \end{pmatrix}$$

METHOD AND DEVICE FOR GEOMETRY ANALYSIS AND CALIBRATION OF VOLUMETRIC IMAGING SYSTEMS

BACKGROUND

The invention relates generally to volumetric imaging systems and more particularly to methods and device for the geometrical analysis and calibration of volumetric imaging systems.

Volumetric imaging systems are utilized for various applications in both medical and non-medical fields. These imaging systems may include for example C-arm, tomosynthesis, computed tomography (CT) imaging systems having varying topologies and are used to create volumetric images or views of a patient based on the attenuation of radiation passing through the patient. Based on the attenuation of the radiation, the topology of the imaging system, and the type and amount of data collected, different views may be constructed, including views showing motion, contrast enhancement, volume reconstructions, two-dimensional images and so forth. Alternatively, volumetric imaging systems may also be utilized in non-medical applications, such as in industrial quality control or in security screening of passenger luggage, packages, and/or cargo. In such applications, acquired data and/or generated images representing volumes or parts of volumes (e.g., slices) may be used to detect objects, shapes or irregularities which are otherwise hidden from visual inspection and which are of interest to the screener.

Some volumetric imaging systems, both medical and non-medical, utilize a radiation source to generate the radiation beam such as X-ray beam and a detector to detect the attenuated signals. The source and/or the detector may move with respect to each other and/or the imaged object, or they may remain stationary. The beam passes through the object being imaged, such as a patient. The radiation beam, after being attenuated by the object impinges upon a detector consisting of an array of detector elements. The intensity of the radiation received at the detector array is dependent upon the attenuation of the radiation beam by the object. Each detector element of the array produces a separate electrical signal that is a measurement of the beam intensity at the detector element location. The intensity measurements from all the detector elements are acquired separately to produce a transmission profile, commonly referred to as projection image.

With the introduction of multi-row and volumetric imaging scanners, including gantry-based and benchtop-type scanners, it has become necessary to determine critical alignment parameters beyond those necessary for traditional two-dimensional scanners. Without these critical alignment parameters, it is difficult or impossible to obtain adequate image quality from a scanner, as the image reconstruction process requires an accurate knowledge of scanner geometry to avoid artifacts and blurring in reconstructed images. Furthermore, in some volumetric imaging systems, it is necessary to physically adjust the locations and/or orientations of the various components to properly align the imaging system.

To obtain good qualitative, or even quantitative reconstruction images, parameters of each viewpoint must be accurately known. A viewpoint pertains to the location and orientation of the various system components with respect to the object. Estimating the parameters directly, i.e. for example by making direct measurements on the acquisition system, is often very difficult and the results can be imprecise.

The term "geometrical calibration of an imaging system" denotes the operation that leads to precise indirect knowledge of the geometrical parameters (well known geometrical parameters include but are not limited to, tube and/or detector position and/or orientation, relative to the imaged object, or relative to a reference coordinate system) that play a role in the production of an image. The underlying principle is based on the use of a geometrical phantom that is (at least partially) known in the 3D space and whose projection image is acquired. The geometrical parameters are then identified based on information extracted from the image.

For single slice CT scanner, it is known that all relevant parameters for alignment can be determined from a single scan of one or two point-like objects or pins. "Pin scans" can be used to extract the magnification of a CT system as well as the center of rotation in a straightforward manner. This technique is specific to single slice CT scanners, since it assumes certain characteristics of the scanning trajectory. It is, however, not applicable to volumetric scanners, for which a number of additional parameters are required.

For high quality 3D reconstruction from a set of projection images, e.g., in X-ray, very accurate information about the acquisition geometry for each projection image is required. In CT, for example, this information is typically available, since the geometric specifications of the gantry are well known, and the mechanics of the gantry and the synchronization with the image acquisition are tightly controlled. However, in other scenarios, e.g., the acquisition of projection data with systems that were originally designed for pure 2D imaging, the system mechanics may be less well defined (e.g., due to mechanical deformability of the gantry), and the synchronization of the image acquisition with the gantry position may also be less accurate. If, however, the geometry of a 3D spin acquisition is repeatable (although not accurately known beforehand, without a calibration), or if the calibration data can be acquired concurrently with the image information of the imaged object, then the conditions for a calibration according to the current invention, are satisfied. This general scenario may apply to mobile C-arm systems (as typically employed for surgical imaging), to fixed-room C-arm systems (e.g., systems for cardiovascular imaging), and also to tomosynthesis-type imaging systems. In these situations, a geometric system calibration may be required for generating images of improved quality.

Current techniques for calibrating/aligning volumetric scanners include the use of phantoms of special construction. These phantoms use a series of small physical balls (e.g., spherical "BBs") or markers in a well-defined, highly accurate spatial configuration, thus allowing for a full geometry calibration for a single view (e.g., calibration using a helix phantom where BBs are located on a helix at a surface of a cylinder, which is placed such that the axis of the cylinder approximately coincides with the axis of rotation of the gantry), as well as other, similarly configured phantoms, maybe containing a smaller number of markers, that allow for a constrained calibration in conjunction with additional system information (e.g., ring containing BBs, where object/anatomy to be imaged is placed within the ring such that partial geometry information is acquired concurrently with the projection images to be used for the 3D reconstruction). The projection image of the phantom may then be used to extract the exact system/imaging geometry at each view position, thus providing the required geometrical information for image reconstruction or system alignment (if the phantom uses a sufficient number of BBs, and the phantom is otherwise matched to the system geometry). However, such phantoms and the associated computational approaches work reliably only over a limited range of imaging geometries (tube and detector position and orientation). In particular, the diameter of the cylinder and pitch of the helical matrix of the phantom limit the utility of such phantoms to a narrow range of magnifications and cone angles.

It is therefore desirable to provide phantom design and calibration methods for volumetric imaging systems to determine the acquisition parameters with greater accuracy so as to generate better images.

BRIEF DESCRIPTION

Briefly in accordance with one aspect of the present technique, a method is provided for geometrical calibration of a volumetric imaging system. The method provides for computing a projection error between estimated locations of a set of markers of a phantom based on a estimated imaging geometry and observed locations of the respective markers for at least one projection image, decomposing the computed projection error into one or more error components corresponding to respective parameters of the imaging geometry, and updating at least one parameter of the estimated imaging geometry based on the one or more error components. Systems and computer programs that afford functionality of the type defined by this method may be provided by the present technique.

In accordance with another aspect of the present technique, a method is provided for geometrical calibration of a volumetric imaging system. The method provides for acquiring a plurality of projection images of a phantom. The phantom comprises a set of markers. The method also provides for identifying true locations of the markers in each of the plurality of projection images, establishing an initial estimate of the imaging geometry, establishing estimated locations of the markers, computing a projection error between the estimated locations of the markers and the true locations of the respective markers for at least one projection image, decomposing the computed projection error into one or more error components corresponding to respective parameters of the imaging geometry, and updating at least one parameter of the estimated imaging geometry based on the one or more error components. Systems and computer programs that afford functionality of the type defined by this method may be provided by the present technique.

In accordance with a further aspect of the present technique, a phantom is provided for a volumetric imaging system. The phantom includes an essentially transparent or partially transparent supporting structure, and a plurality of discrete, essentially opaque markers spaced apart from one another on or within the supporting structure. The markers are arranged in a helical array such that the slope of the helix increases from the center of the supporting structure towards the end of the supporting structure.

In accordance with an additional aspect of the present technique, a phantom is provided for a volumetric imaging system. The phantom includes an essentially transparent or partially transparent supporting structure, and a plurality of discrete, essentially opaque markers spaced apart from one another on or within the supporting structure. The markers are arranged in a helical array such that the radius of the helix decreases from the center of the supporting structure towards the end of the supporting structure.

In accordance with another aspect of the present technique, a phantom is provided for a volumetric imaging system. The phantom includes an essentially transparent or partially transparent supporting structure, and a plurality of discrete, essentially opaque markers spaced apart from one another on or within the supporting structure. The markers are arranged in an elongated pattern. The phantom also includes a plurality of elongated patterns of markers rotationally offset from each other.

In accordance with a further aspect of the present technique, a phantom is provided for a volumetric imaging system. The phantom includes an essentially transparent or partially transparent supporting structure, and a plurality of discrete, essentially opaque, rod-shaped markers spaced apart from one another on or within the supporting structure. A subset of markers is arranged in an elongated pattern.

DRAWINGS

These and other features, aspects, and advantages of the present invention will become better understood when the following detailed description is read with reference to the accompanying drawings in which like characters represent like parts throughout the drawings, wherein:

FIG. 5 depicts a matrix containing the vectors associated with the error components that correspond to specific parameters of the imaging geometry, as illustrated in FIG. 4;

Figure 6:
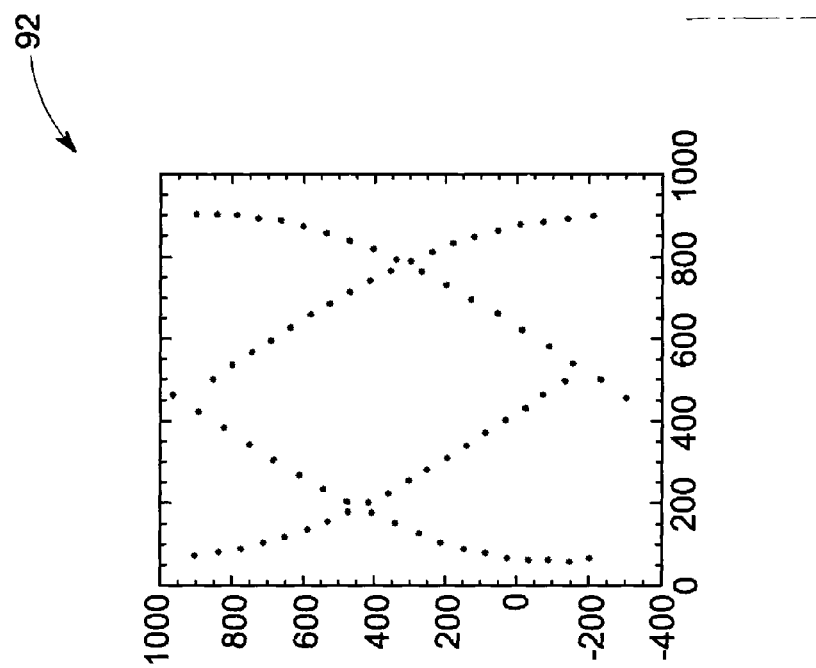
Figure 6:
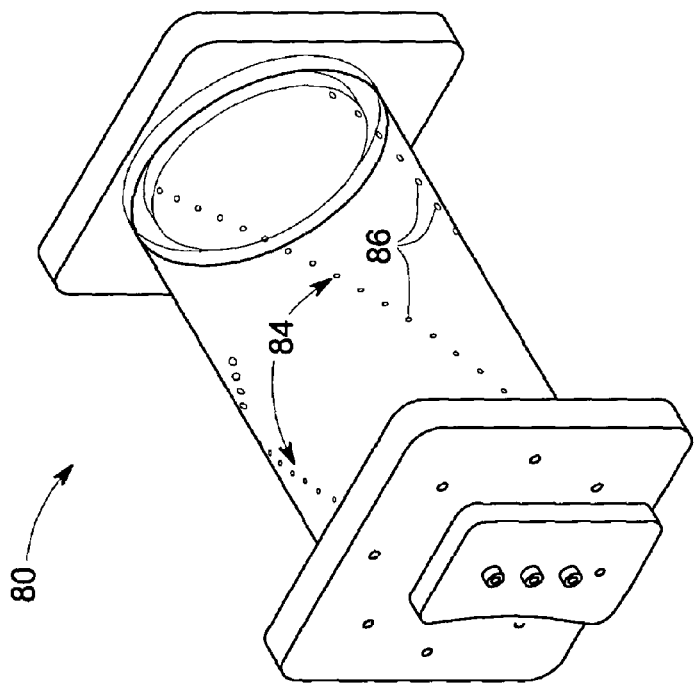
Figure 7:
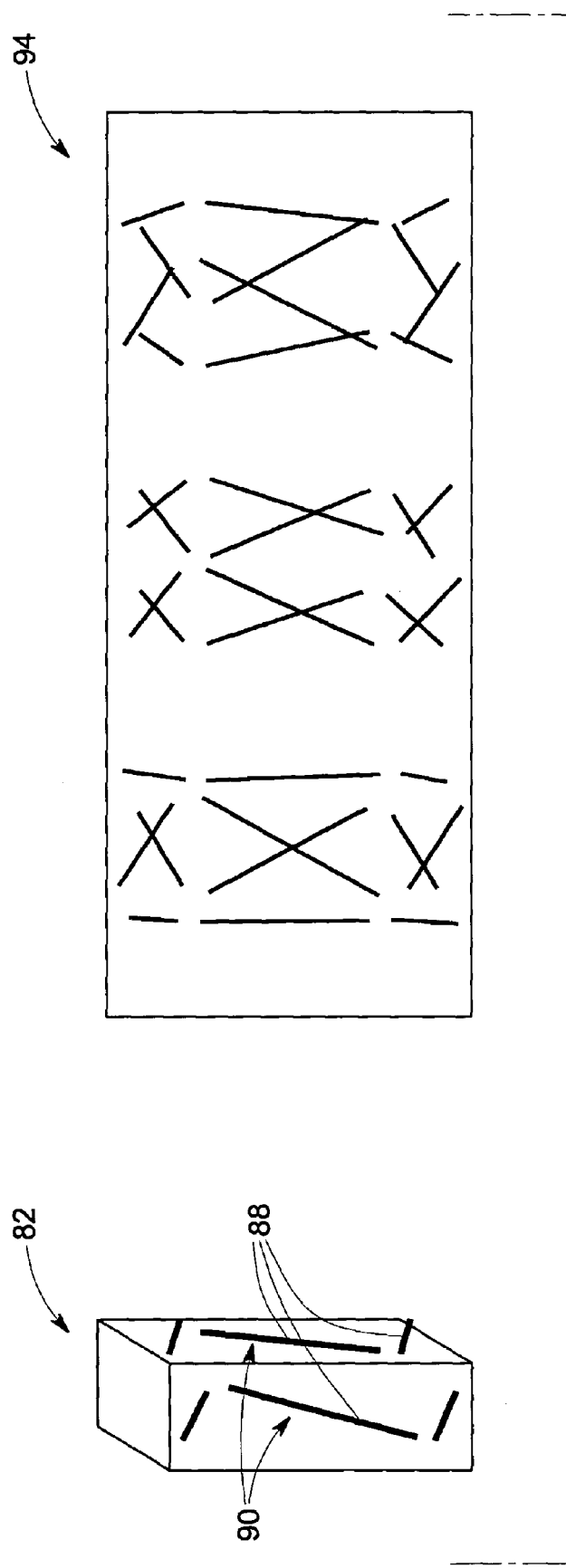

FIG. 6 depicts a "candy cane" phantom with a set of helical elongated patterns that are rotationally offset from each other, and a graph illustrating the "candy cane" phantom in a projection image; and FIG. 7 depicts another phantom design with rod markers arranged in an elongated pattern, where multiple such patterns are rotationally offset from each other, and a graph illustrating the phantom in three projection images from three different angles.

DETAILED DESCRIPTION

The present techniques are generally directed to geometrical analysis and calibration of volumetric imaging systems. Such analysis and calibration techniques may be useful in a variety of imaging contexts, such as CT imaging, CT metrology, industrial inspection systems, tomosynthesis, C-arm systems and others. Though the present discussion provides examples in a CT imaging context, one of ordinary skill in the art will readily apprehend that the application of these techniques in other contexts, such as for industrial imaging, and/or tomosynthesis, is well within the scope of the present techniques.

Figure 1:
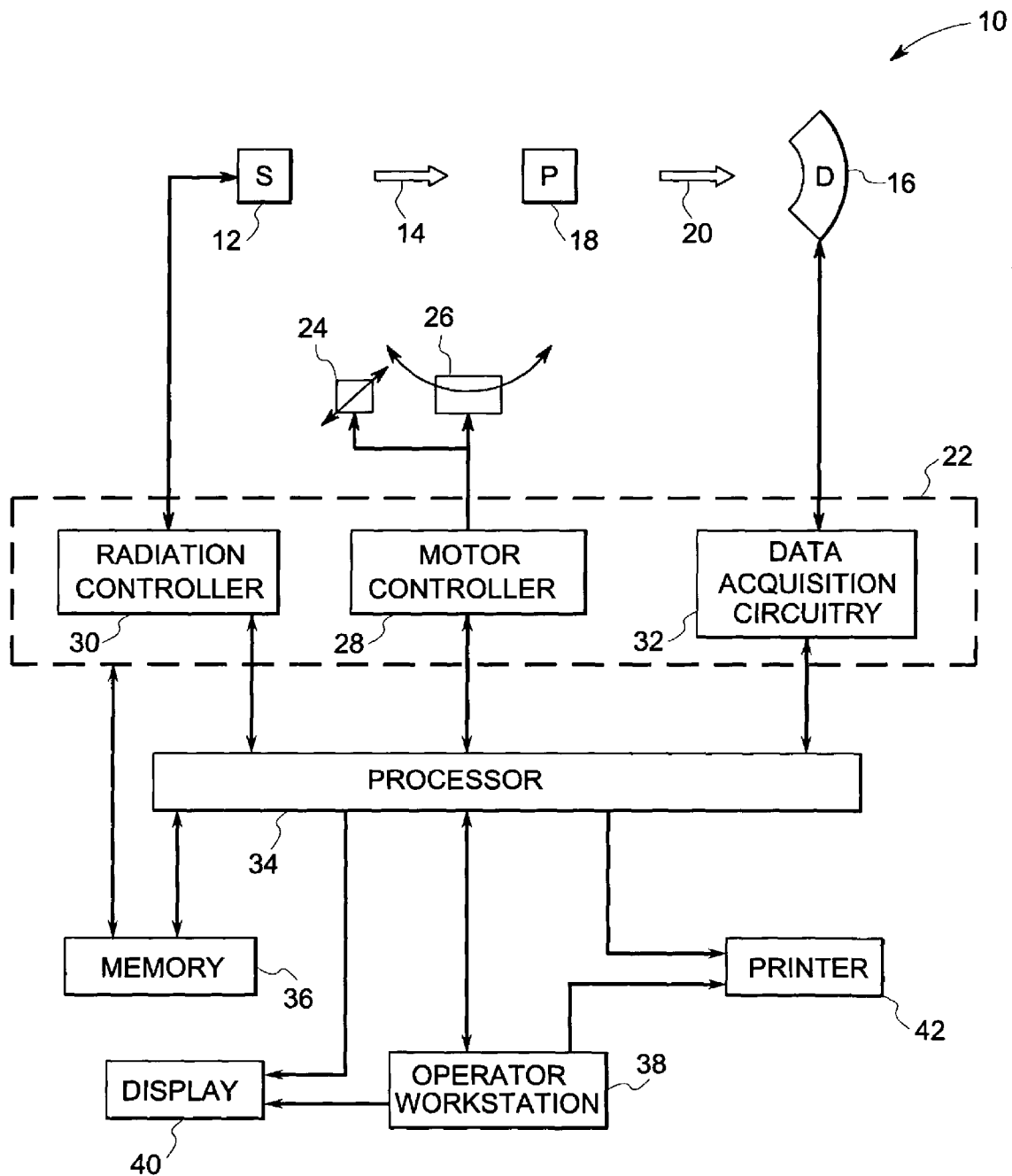
FIG. 1 is a diagrammatical representation of an exemplary volumetric imaging system for geometrical analysis and calibration in accordance with one aspect of the present technique.

Referring now to FIG. 1, an imaging system 10 for use in accordance with the present technique is illustrated. In the illustrated embodiment, the imaging system 10 includes a radiation source 12, such as an X-ray source. A collimator may be positioned adjacent to the radiation source 12 for regulating the size and shape of a stream of radiation 14 that emerges from the radiation source 12. In typical operation, the radiation source 12 projects a stream of radiation 14, such as X-rays, towards a detector array 16 placed on the opposite side of the radiation source 12, relative to the imaged patient/object. The stream of radiation 14 passes into an imaging volume in which an object or a patient 18 to be imaged may be positioned. It should be noted that a particular region of the object or the patient 18 may be chosen by an operator for imaging so that the most useful scan of the region may be acquired.

A portion of the radiation 20 passes through or around the object or the patient and impacts the detector array 16. The detector array 16 may be an area detector and is generally formed as a two-dimensional array of detection elements. Each detector element produces an electrical signal that represents the intensity of the incident radiation 20 at the detector element when the radiation 20 strikes the detector array 16. Typically, signals are acquired at one or more view angle positions around the object or the patient 18 so that a plurality of radiographic views may be collected. These signals are acquired and processed to reconstruct an image of the features internal as well external to the object or the patient 18.

The object or the patient 18 and the radiation source 12 are typically displaced relative to each other, allowing projection data to be acquired at various views relative to the object or the patient 18 if desired. For example, the object 18 may be positioned on a table, such as a turntable, so that the object 18 may be rotated during the examination process to expose the object 18 to the stream of radiation 14 from all sides. Alternatively, the radiation source 12 and/or the detector array 16 may be disposed on a gantry, which may be rotated around the object or the patient 18 placed on a table during the examination process. Further, in certain embodiments, components of the imaging system as well as the imaged object may be moved during the examination process to acquire projection images at different views. As the object or the patient 18 and the radiation source 12 rotate relative to each other, the detector array 16 collects data of radiation attenuation at the various view angles relative to the object or the patient 18.

Data collected from the detector array 16 then typically undergoes pre-processing to condition the data to represent the line integrals of the attenuation coefficients of the scanned objects or patient 18. The processed data, commonly called projections, are then reconstructed to formulate a volumetric image of the scanned area, as discussed in greater detail below.

Operation of the source 12 is controlled by a system controller 22, which furnishes both power, and control signals for examination sequences. Moreover, the detector array 16 is coupled to the system controller 22, which commands acquisition of the signals generated in the detector array 16. The system controller 22 may also execute various signal processing and filtration functions, such as for initial adjustment of dynamic ranges, interleaving of digital image data, and so forth. In general, the system controller 22 commands operation of the imaging system 10 to execute examination protocols and to process acquired data. In the present context, system controller 22 may also include signal processing circuitry and other circuitry, typically based upon a general purpose or application-specific digital computer, with associated memory circuitry. The associated memory circuitry may store programs and routines executed by the computer, configuration parameters, image data, and so forth. For example, the associated memory circuitry may store programs or routines for implementing the present technique.

In the embodiment illustrated in FIG. 1, the system controller 22 is coupled to a linear positioning subsystem 24 and a rotational subsystem 26. In particular, the system controller 22 may include a motor controller 28 that controls the operation of the linear positioning subsystem 24 and the rotational subsystem 26. The rotational subsystem 26 enables the X-ray source assembly and/or the detector assembly to be rotated around the object or the patient 18. It should be noted that the rotational subsystem 26 may include a gantry. Thus, the system controller 22 may be utilized to control the rotational speed and position of the gantry. Alternatively, the rotational subsystem 26 may include a motorized turntable and the system controller 22 may be configured to rotate the motorized turntable, thereby rotating the object 18 one or multiple turns during an examination. The linear positioning subsystem 24 enables the object 18 to be displaced linearly, such as by moving a table or support on which the object 18 rests. Thus, in one embodiment, the table may be linearly moved within a gantry to generate images of particular areas of the object or the patient 18. In another embodiment (e.g., in a tomosynthesis system), the X-ray source may be moveable using a linear positioning subsystem. The detector position may be variable, but not be controlled using a positioning subsystem. It should be noted that other configurations may also be used.

Additionally, as will be appreciated by those skilled in the art, the radiation source 12 may be controlled by a radiation controller 30 disposed within the system controller 22. Particularly, the radiation controller 30 may be configured to provide power and timing signals to the radiation source 12. Further, the system controller 22 may include data acquisition circuitry 32. In this exemplary embodiment, the detector array 16 is coupled to the system controller 22, and more particularly to the data acquisition circuitry 32. The data acquisition circuitry 32 typically receives sampled analog signals from the detector array 16 and converts the data to digital signals for subsequent processing by a processor 34. Such conversion, and indeed any preprocessing, may actually be performed to some degree within the detector assembly itself.

The processor 34 is typically coupled to the system controller 24. Data collected by the data acquisition circuitry 32 may be transmitted to the processor 34 for subsequent processing and reconstruction. Reconstruction of the image may be done by general or special purpose circuitry of the processor 34. Once reconstructed, the image produced by the imaging system 10 reveals internal as well as external features of the object or the patient 18. Alternatively, an image reconstructor, that is coupled to or is a part of a processor 34, may receive sampled and digitized data from the data acquisition circuitry 32 and may perform high-speed image reconstruction to generate one or more images of the scanned object or patient 18.

The processor 34 may include or be in communication with a memory 36. It should be understood that any type of computer accessible memory device suitable for storing and/or processing such data and/or data processing routines may be utilized by such an exemplary imaging system 10. Moreover, the memory 36 may comprise one or more memory devices, such as magnetic or optical devices, of similar or different types, which may be local and/or remote to the system 10. The memory 36 may store data, processing parameters, and/or computer programs comprising one or more routines for performing the processes described herein. Furthermore, memory 36 may be coupled directly to system controller 24 to facilitate the storage of acquired data.

The processor 34 is typically used to control the imaging system 10. The processor 34 may also be adapted to control features enabled by the system controller 22, i.e., scanning operations and data acquisition. Indeed, the system controller 22 may be implemented as hardware and software components of the depicted processor 34. In addition, the processor 34 may be configured to receive commands and scanning parameters from an operator via an operator workstation 38.

For example, the operator workstation 38 may be equipped with a keyboard and/or other input devices by which an operator may control the imaging system 10. Thus, the operator may observe the reconstructed image and other data relevant to the system from processor 34, initiate imaging and so forth. Where desired, other computers or workstations may perform some or all of the functions of the present technique, including post-processing of image data simply accessed from memory device 36 or another memory device at the imaging system location or remote from that location.

A display 40 may be coupled to one of the operator workstation 38 and the processor 34 and may be utilized to observe the reconstructed image and/or to control imaging. Additionally, the scanned image may also be printed by a printer 42 which may be coupled to the processor 34 and/or the operator workstation 38, either directly or over a network. It should be further noted that the processor 34 and/or operator workstation 38 may be coupled to other output devices that may include standard or special purpose computer monitors and associated processing circuitry. Furthermore, additional operator workstations may be further linked in the imaging system 10 for outputting system parameters, requesting inspection, viewing images, and so forth, so that more than one operator may perform operations related to the imaging system 10. For example, one operator may utilize one operator workstation to image acquisition while a second operator utilizes a second operator workstation to reconstruct and/or review the results of the imaging routines. In general, displays, printers, workstations, and similar devices supplied within the imaging system 10 may be local to the data acquisition components, or may be remote from these components linked to the imaging system 10 via one or more configurable networks, such as the Internet, virtual private networks, and so forth.

As will be appreciated by one skilled in the art, the geometric parameters of the volumetric imaging system 10 may be obtained utilizing a scan of a calibration phantom and calibrating techniques. General calibration techniques include the acquisition of one or more projection images where specific markers or structures of the phantom are visible (or detectable) in the image. It should be noted that these markers may also be anatomical markers, i.e., "salient" features or landmarks within the imaged volume. Further, it should also be noted that not all markers need to be visible in any one projection image; generally, some subset of markers may be sufficient. An initial (possibly very rough) estimate of the imaging geometry (which includes tube and detector position and orientation) is updated iteratively to achieve an optimal estimate of the imaging geometry. As will be appreciated by one skilled in the art, in certain embodiments, the imaging geometry is defined relative to the position and orientation of the calibration phantom. It should be noted that the term imaging geometry is used here to refer to both the imaging geometry associated with a single projection image, as well as the collection of imaging geometries associated with the acquisition of a plurality of projection images.

Figure 2:
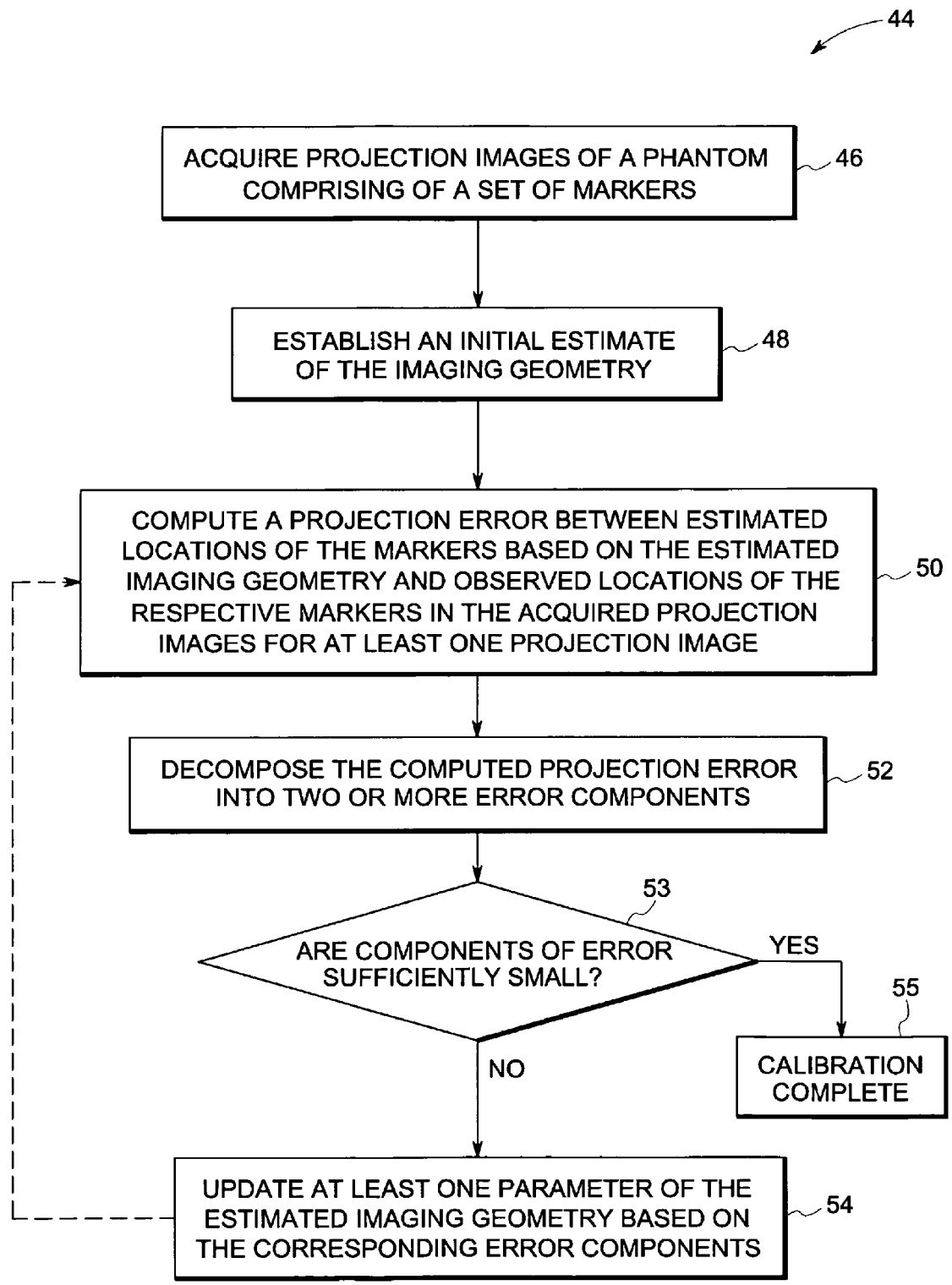
FIG. 2 is a flowchart illustrating an exemplary process for geometrical calibration of a volumetric imaging system in accordance with one aspect of the present technique.

For example, referring now to FIG. 2, exemplary control logic 44 for geometrical analysis and calibration of volumetric imaging systems such as imaging system 10 is depicted via a flowchart in accordance with aspects of the present technique. As illustrated in the flowchart, exemplary control logic 44 includes the steps of acquiring one or more projection images of a phantom (comprising a set of markers) at step 46, establishing an initial estimate of the imaging geometry at step 48, and computing a projection error between estimated/predicted locations of the marker shadows based on the estimated imaging geometry and true/observed locations of the respective marker shadows in the acquired projection images for at least one projection image at step 50. The control logic 44 further continues by decomposing the computed projection error into two or more error components, where at least one of the components corresponds to respective geometric parameters of the imaging geometry at step 52. Generally, the decomposition is such that each of the two or more error components (with the exception of a residual error component) corresponds to a single specific parameter of the imaging geometry. It should be noted that the two or more error components may also include a "residual" component, which captures the component of the error not associated with any of the specific parameters considered. The control logic 44 then checks to determine whether the components of the error that are associated with respective parameters of the imaging geometry are sufficiently small at step 53. If the error components are not sufficiently small, the control logic 44 updates at least one geometric parameter of the estimated imaging geometry based on the corresponding error components at step 54 and goes back to step 50. As will be appreciated by one skilled in the art, the geometric parameters of the imaging geometry may then be iteratively updated by iterating the steps 50, 52 and 54. It should be noted that the geometric parameters are selectively updated in each iteration (i.e., for different iterations different parameters may be updated). For example, in initial iterations only some parameters may be updated, and in latter iterations, all parameters may be updated. Once the error components are sufficiently small the control logic 44 completes the calibration process at step 55.

Figure 3:
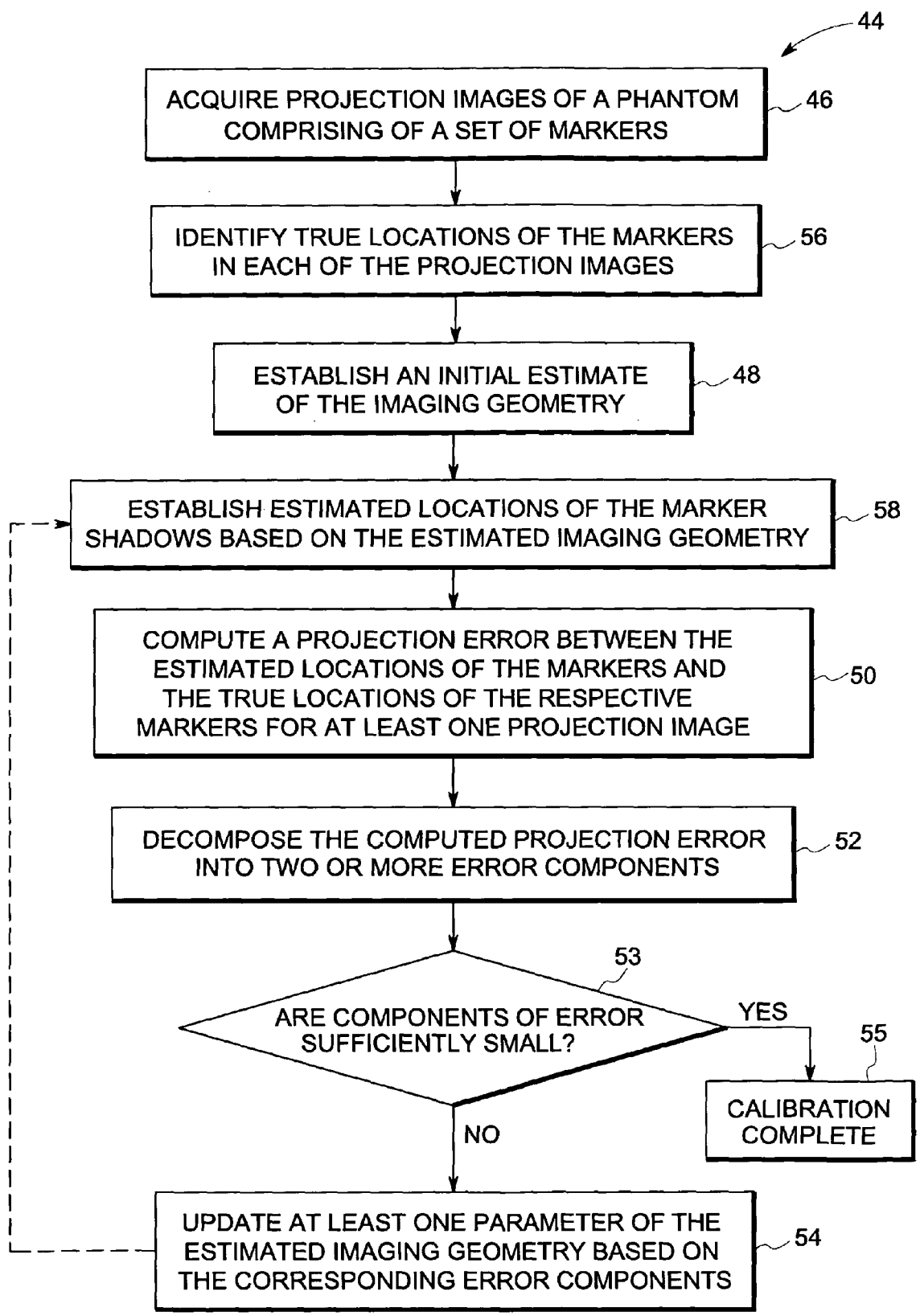
FIG. 3 is a flowchart illustrating the exemplary process of FIG. 2, in greater detail and in accordance with one aspect of the present technique.

By means of further example, the geometrical analysis and calibration technique of volumetric imaging systems illustrated in FIG. 2 may further be elaborated as shown in FIG. 3. In the illustrated control logic set forth in FIG. 3, one or more projection images of the phantom are acquired at step 46. The true/observed locations of the marker shadows are then identified in each of the plurality of projection images at step 56. Further, an initial estimate of the imaging geometry is established at step 48 and estimated/predicted locations of the projected markers are established based on the estimated imaging geometry at step 58. The projection error between the estimated locations of the markers and the true locations of the respective markers is then computed for at least one projection image at step 50. The computed projection error is decomposed into two or more error components at step 52. The control logic 44 then checks to determine whether the components of the error that are associated with respective parameters of the imaging geometry are sufficiently small at step 53. If the error components are not sufficiently small, one or more geometric parameters of the estimated imaging geometry are updated based on the corresponding error components at step 54. The control logic 44 then goes back to step 58. The geometric parameters of the imaging geometry may then be iteratively updated by iterating the steps 58, 50, 52 and 54. Once the error components are sufficiently small the calibration process is completed at step 55.

Figure 4:
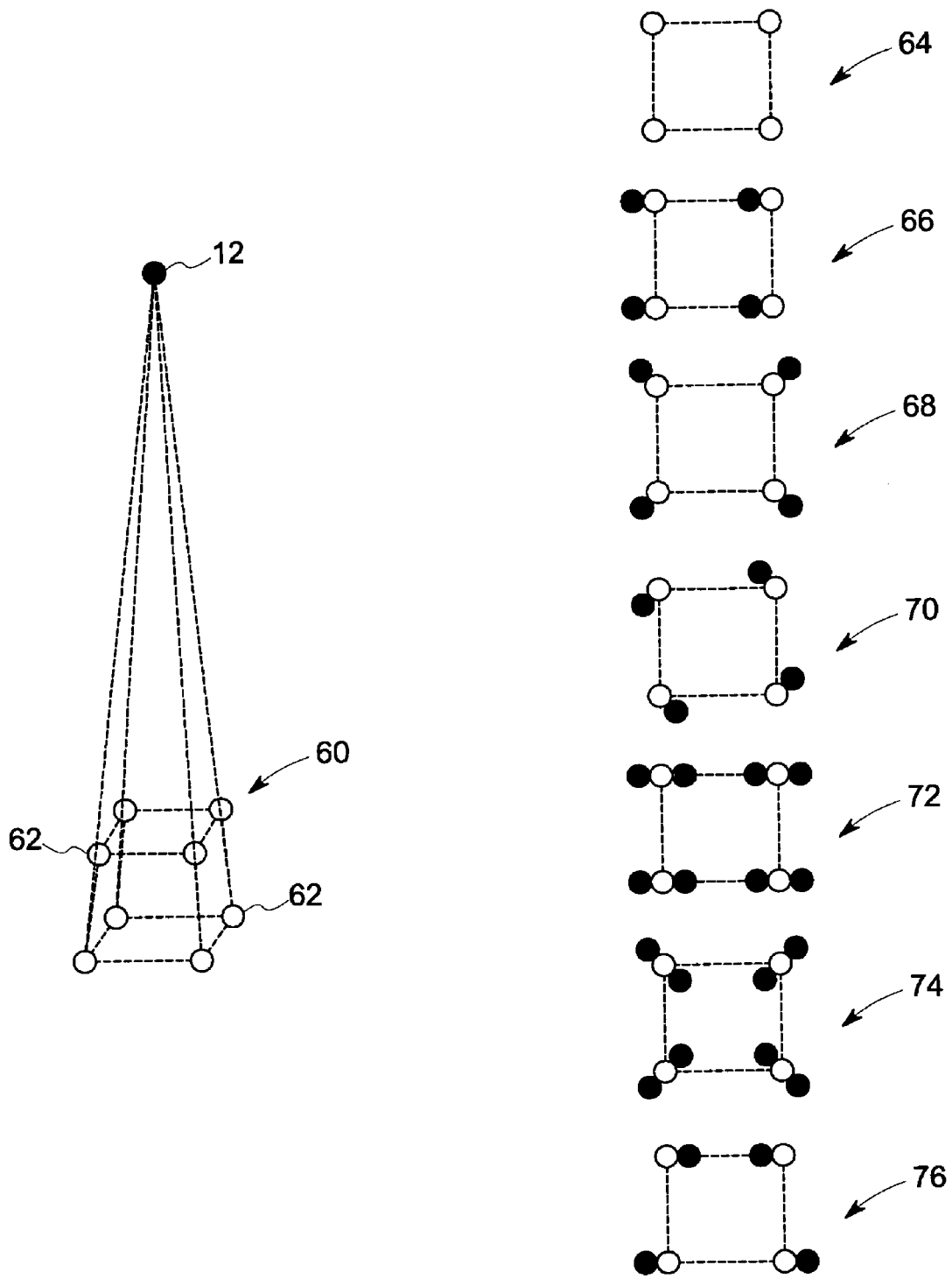
FIG. 4 depicts error components associated with specific parameters of the imaging geometry.

As mentioned above, the calibration approach of the present technique is enabled due to a specific relationship between projection error components and the parameters that define the system geometry. This specific relationship is explained in greater detail with reference to FIG. 4. For example, let us assume that the phantom 60 consists of eight markers 62, arranged at the corners of a "slightly deformed" cube as illustrated in FIG. 4, such that for the true imaging geometry pairs of markers 62 are projected onto the same location on the detector. It should be noted that the cube as shown is 'slightly deformed', otherwise the projections of the markers would not be superimposed for all four pairs of markers. In the illustrated configuration, the projection shadows 64 of the markers will be found at four different locations at the corners of a square (at each location, the shadows of two markers are superimposed). The projections of the markers, and the projections of the centers of the markers are referred to as "shadows".

However, if the estimated imaging geometry differs from the true geometry, then the locations of the shadows of the markers will be at different locations on the detector, and this error will have different characteristics, depending on what parameter of the imaging geometry causes that error. Some different errors in specific imaging geometry parameters as well as the associated error components in the projection image are shown in FIG. 4. As shown in FIG. 4, the unshaded marker shadows represent the true or known marker shadow locations of the phantom and the shaded marker shadows represent the corresponding locations associated with the estimated imaging geometry (which differs from the true imaging geometry). Therefore, the shaded marker shadows are shown to be shifted/offset from the true or actual marker shadow location based on the different error types. The first error type 66 that is shown is associated with a translational error of the detector position, where that translation is "horizontal" (i.e., in a plane parallel to the detector itself). There is a similar error (not shown) for a translation of the detector in the other horizontal direction leading to second error type. The third error type 68 that is illustrated is a scaling of the projection image, which is associated with a translation of the detector in a direction orthogonal to the detector plane. The forth error type 70 is associated with a (planar) rotation of the detector. The fifth error type 72 is associated with a horizontal (i.e., parallel to the detector plane) translation of the source position (i.e., the focal spot). Moving the source in this manner will lead to two different effects. First, this translation of the source will cause an overall translation in the shadows of the markers; and second, it will lead to a relative translation of the shadows of the markers associated with the top layer of the phantom vs. the shadows of the markers associated with the bottom layer of the phantom. Only the second component of the error, which is specific to the horizontal translation of the source, is illustrated here. There is a corresponding error component (not shown) for a translation of the source position in the other horizontal direction leading to sixth error type. The seventh error type 74 is associated with a vertical translation of the source (i.e., orthogonal to the detector plane). This leads to an overall scaling of the projection image (not shown) as well as a change in the relative scaling between the images of the top layer of the phantom, and the bottom layer of the phantom. This second component of the error is specific to the vertical translation of the source. The eighth type of error 76 is associated with a tilt of the detector. This leads in effect to a spatially varying magnification factor (due to the spatially varying detector to object distance), as illustrated in FIG. 4, where the magnification factor at the "top of the detector" is smaller than the magnification factor at the "bottom of the detector". Again, this error component has a counterpart for a detector tilt in the other direction (not shown) leading to a ninth error type.

All degrees of freedom of the imaging system have therefore a different associated specific error component. Thus, there is a specific error component associated with each of the parameters defining the 3D position of the source (translation in both horizontal directions, as well as in the vertical direction), the 3D position of the detector (translation in both horizontal directions as well as vertical) and the 3D orientation of the detector (in-plane rotation, as well as tilt in two directions).

When analyzing these error components, it can be shown that these different specific error components are independent of each other (i.e., no error component can be replicated by using some combination of the other error components). The error components may be further translated in vector format to facilitate easy analysis. For example, when formally writing down the specific errors discussed above in vector format, where for each marker we have two vector elements, one for the x- and one for the y-direction (i.e., the axes that span the detector plane), a vector matrix 78 as illustrated in FIG. 5 may be obtained, where each column of the matrix corresponds to one of the error types, as discussed above. As will be appreciated by one skilled in the art, these error vectors are indeed linearly independent. While the errors as shown in the matrix 78 in FIG. 5 are orthogonal, the error vectors for more general phantoms, and/or other imaging geometries relative to the imaged phantom, will generally be at least linearly independent. Therefore, the calibration method of the present technique may be used with a wide variety of phantoms, or with a wide variety of spatial arrangements of markers. A family of calibration phantoms that are suitable for the above mentioned calibration techniques, but which may also be used in conjunction with other calibration techniques, are described in greater detail below.

As will be appreciated by one skilled in the art, the shown correspondences between specific parameters describing the imaging system geometry and components of the re-projection error are not intended to constrain the present technique. Other parametrizations of the system geometry may also be possible, leading to other associated error components (which, however, will still be linearly independent). It should be noted that the "error vectors" 78 as illustrated in FIG. 5 correspond in fact to the columns of the Jacobian matrix of the coordinates of the marker shadows as a function of deviations in the parameters of the imaging geometry, and can be computed, for example, analytically, or through finite differences.

Depending on the markers in the specific phantom that is used, other error terms may be used as well. In the example above, the error vectors are composed of the reprojection error of each marker along both detector coordinate axes. The error terms that are collected in the error vector may also consist of only the x- or only the y-component of the individual errors, with only a single error component for some, or all of the markers. In another example, the calibration phantom may consist of rods. Here, the error terms may consist of the error in a direction orthogonal to the edge of the rod (as seen in the projection image). Thus, only the location/orientation of the linear edge (which can be detected with high accuracy) has an impact on the calibration result, whereas the endpoints of the edge (which can be detected only less accurately) do not have a significant impact on the calibration. One may want to use such an error term near each end point of a rod. This more general error term may also be used, for example, when separate markers are used that are spatially arranged in a linear relationship (i.e., along a line). Other than linear structures, e.g., smooth curves in 3D may also be used. In this case the error terms may also be given by the deviations from the curve, in a direction that is locally orthogonal to that curve. This same type of error may be used, for example, when bigger shapes are used as elements of the phantom. For example, if large spherical markers are used, the elliptical outline of the shadow may be used as "indicator" of the projected image, and the error term may consist of the local error in a direction locally orthogonal to the outline. If a polygonal plate is used in the phantom, the error may consists of the "point-type" errors, for example for the projections of the corners of the plate, or the error may consist of the error in a direction orthogonal to the projected edges, or some combination thereof. It should be noted that for "hybrid" phantoms, containing more than one type of markers and/or spatial arrangements of markers that are amenable to different kinds of error, different error types, including "hybrid" error vectors, may be used. Further, it should be noted that at different iteration steps, different error vectors (maybe consisting of different types of error terms) may be used. As will be appreciated by one skilled in the art, the embodiments or techniques described herein may also be used, for example, to evaluate phantom performance (i.e., specific phantom designs can be compared, and their relative performance evaluated).

The decomposition of the error may be done in several different ways. In one embodiment, decomposition of the observed error into components that are associated with specific parameters of the imaging geometry is based on a suitable Taylor-like expansion around the current estimate, using the Jacobian matrix or an approximation thereof. For example, for the current estimate of the geometry and the current estimate of the marker locations, the error vector that is associated with a variation in a single specific geometry parameter may be determined. By doing this for all geometry parameters, the corresponding independent error vectors may be obtained, and the observed error vector can be decomposed into a linear combination of these error vectors, e.g., by using a least-squares fit. Some or all elements of the solution to this least-squares fit may then be used to update the current estimate of the geometry. In one embodiment, this update step represents in fact a Newton step.

Other approaches may be empirical, that is, the decomposition may be entirely "image based". For example, the mean component of the error defines the detector translation. The center of mass of the points may serve as a point of reference for determining a scaling component (i.e., if all error vectors "point away" from the reference point, then the scaling component, associated with the vertical detector translation, needs to be adjusted correspondingly). This same reference point may be used to estimate, e.g., detector rotation, vertical translation of focal spot, etc. in a suitable way.

In this image based approach, to map the error decomposition to an update of the geometry parameters, the values for the current estimate of the imaging geometry need to be taken into account. For example, the current estimate of the imaging geometry in conjunction with the estimated location of the markers is associated with a certain magnification factor. The scaling component of the error defines a relative change in the magnification, i.e., the new magnification is based on the current estimate, which is then appropriately updated using information from the corresponding error component.

Other approaches to decomposing the error vector, and updating the estimated imaging geometry may be used as well. These include "black box" approaches that do not explicitly take the relationship between geometry parameters and reprojection error into account, but determine an optimal estimate of the imaging geometry by some search strategy that aims at finding the minimum of the optimization criterion. Any of the mentioned update strategies may also include techniques for better management of noisy observations or outliers in the data, e.g., total least squares approaches, techniques from robust statistics, and so forth.

When decomposing the error and updating the current estimate of the imaging geometry, it should be noted that while considering some parameters (such as the error components corresponding to a detector tilt, and a vertical translation of the focal spot) the current estimate of most other geometry parameters are assumed to be fairly accurate. Therefore, in some embodiments, and depending on the characteristics of the specific calibration task, in the first steps of the iteration (depending on the accuracy of the estimates in these first steps) the corresponding parameters may not be updated and nominal values for these parameters may be assumed, or they may be assumed to suitably track other geometry parameters. For example, in a C-arm system, the detector orientation/tilt may initially be updated such that the detector is orthogonal to a line through the estimated/updated focal spot location and the estimated center of rotation. Once this initial constrained optimization is performed, the detector tilt and the source-detector distance may be updated (separately, or concurrently with an update of other imaging parameters) in subsequent steps.

Several variations of the above mentioned calibration technique may be employed for geometrical analysis and calibration of the volumetric imaging system. For example, in one embodiment, the calibration method of the present technique employs a phantom with accurately known marker locations (in 3D). The method includes the steps of acquiring one or more projection images, where each image contains the image (i.e., the shadows) of a set of markers of the phantom, and identifying marker locations in the images (i.e., determining location of marker shadows within the image, and establishing a correspondence between markers in the image and markers in the phantom). The method further include the steps of establishing an initial estimate of the imaging geometry, reprojecting the marker locations assuming the current estimate of projection geometry and computing reprojection errors for at least one projection image, decomposing the error into error components, and updating at least one associated parameter of the current estimate of the imaging geometry based on respective error component. The method also includes iteratively updating the current estimate of the imaging geometry.

In another embodiment, the calibration method of the present technique includes the steps of acquiring one or more projection images, where each image contains the image (i.e., the shadows) of a set of markers of the phantom, identifying marker shadow locations in the images (i.e., determining location of marker shadows within the image), reconstructing 3D location of markers (i.e., establishing a model of the phantom) based on the current estimate (i.e., nominal configuration) of the projection geometry by backprojecting the detected marker shadow locations and estimating the 3D positions of the markers from these backprojected lines. The method further includes the steps of establishing a correspondence between the phantom model and the reconstructed 3D marker positions, reprojecting the current estimated marker locations (which may be given by the set of estimated marker locations, or by the phantom model, positioned according to the estimated marker positions) assuming the current estimate of projection geometry and computing reprojection errors for at least one projection image, decomposing the error into error components, and updating at least one associated parameter of the current estimate of the imaging geometry based on respective error component. The method also includes iteratively updating the current estimate of the imaging geometry. It should be noted that, in the described embodiment, the correspondence problem (correspondence between the markers in the phantom and the image of the respective markers in the projection images) is solved in the 3D domain, thereby replacing the complexity of that problem with an initial reconstruction step, which assumes that the nominal imaging geometry is approximately known. However, when doing this, the specific geometry and structure of the phantom itself becomes less important, since the phantom design does not need to enable the easy solution of the correspondence problem in the projection image domain. For this same reason, this approach also enables the use of phantoms that are manufactured with lesser accuracy, but may be measured themselves (or "calibrated") beforehand. Further, it should be noted that, the collection of markers may be an almost random arrangement as long as it spans the 3D space to be calibrated.

In yet another embodiment, the calibration method of the present technique include the steps of acquiring one or more projection images, where each image contains the image (i.e., the shadows) of a set of markers of the phantom, identifying marker shadow locations in the images (i.e., determining location of marker shadows within the image, and establishing a correspondence between markers in the image and markers in the phantom), reconstructing estimated 3D locations of markers based on the current estimate of the projection geometry, reprojecting the current estimated marker locations assuming the current estimate of projection geometry and computing reprojection errors for at least one projection image, decomposing the error into error components, and updating at least one associated parameter of the current estimate of the imaging geometry based on respective error component. The method also includes iteratively updating the current estimate of the imaging geometry. It should be noted that the described embodiment has an additional step where the location of markers, i.e., the phantom geometry is updated. This step of reconstructing the estimated 3D location of the markers will typically involve computing an optimal estimate of the intersection of lines in 3D space. A least squares method may be used for this step, where the estimated 3D location of any given marker minimizes the sum of squared distances from that location to the lines that join the 3D position of the shadows of that marker with the corresponding 3D focal spot location of the source for that projection image. An advantage of this approach is the fact that the geometry of the used phantom does not have to be known with very high accuracy, thereby reducing phantom cost. Also, with this approach, the phantom does not need to be calibrated beforehand. However, when using this approach the recovered geometry (both imaging and phantom geometry) is not uniquely determined in the sense that some smooth deformations of the 3D space (including the phantom and imaging geometry) will also produce very small reprojection errors. To produce generally acceptable 3D image quality in 3D reconstructions based on the calibration results, these smooth deformations of 3D space are inconsequential. However, if absolute accuracy of the calibration results is required, then some additional constraints on the phantom may be sufficient to achieve this goal, without requiring high accuracy in the placement of every single marker in the phantom. These additional constraints may include having some special markers in the phantom, (e.g., square plates), the geometry of which is accurately known, or subsets of markers, the relative geometry of which is accurately known. Similar constraints on the imaging geometry may also be used, such as, knowledge of the geometry for a small set of views with very high accuracy.

As will be appreciated by one skilled in the art, the different calibration approaches described above span a wide range of hybrid methods that may leverage different combinations of the core elements of these approaches. For example, a 3D volumetric model of the phantom may be reconstructed without first identifying the marker shadows in the projection images, the markers may then be optionally identified in the reconstructed model, and a correspondence may be established between the 3D model of the phantom and the reconstructed volume. Further, it should be noted that, the various calibration methods of the present technique do not rely on a specific representation of the imaging geometry. For example, projection matrices, or any other suitable representation of the imaging geometry may be used. For an error analysis, and the associated correction of the imaging geometry as described above, the imaging geometry data may be converted to a representation in a suitable form.

For some markers in the phantom, or for specific arrangements of markers in the phantom, the processing in the calibration may also be structured differently. For example, for markers in a linear arrangement, or in an arrangement along a smooth curve, a first stage of the calibration (initial iteration steps) may be based on just identifying and matching the detected curve in the projection images to the corresponding curve in the phantom, followed by a second stage of the calibration (later iteration steps) where individual markers are matched. In other words, different error types and decompositions may be computed in different iterations to update the geometric parameters. In one embodiment described above both geometry parameters and marker locations are updated repeatedly. In other embodiments, the phantom may be well defined, with high accuracy. Thus, only the imaging geometry parameters may be updated. Alternatively, the first step may be used to estimate the correct location/position of the phantom, and then only parameters describing the imaging geometry may be updated. In other embodiments, some aspects of the phantom may be well defined (e.g., distances between some pairs of points), while other aspects are left flexible. In other embodiments, some parameters of the imaging geometry may be constrained (e.g., in tomosynthesis, where the detector typically remains stationary). Here, only the relevant parameters of the geometry are updated. Also, since in one embodiment described above both system geometry and marker locations are estimated, there is no global reference point. By fixing (and not updating) a suitable subset of parameters, all other parameters are estimated relative to these reference points.

With suitable modifications, the approach outlined above may also be used to calibrate different imaging systems, for example systems where the tube and/or detector remain stationary, while the imaged object is rotated and/or translated. This might be particularly applicable to in non-destructive evaluation (NDE).

Further, it should be noted that in some embodiments of the current calibration method the RMS (root mean-square) error between detected marker locations and predicted marker locations (based on the estimated imaging geometry) is minimized. In this context, there generally exists for each acquired projection image a uniquely determined optimal estimate of the imaging geometry. However, in cases where we have additional constraints on the imaging geometry (due to some prior knowledge, e.g., through physical measurements of some of the parameters), this additional constraint may actually be taken into account during the calibration itself. In certain embodiments, it may also be taken into account after the calibration was successfully performed since the present framework allows for an efficient evaluation of such trade-offs (minimize RMS error while satisfying some constraints).

In certain embodiments, the present technique may also be used for 2D to 3D registration, where, for example, a 3D dataset (containing the markers) is acquired, and then a 2D projection image of the object, and the markers is acquired. For example, during surgery planning and surgical navigation it may be beneficial to determine exactly what the imaging geometry of the 2D image acquisition was relative to the 3D dataset. This may be easily achieved with the various embodiments of the present technique.

The step of locating and/or identifying the markers within the projection image or the step of solving the correspondence problem may involve pre-processing the acquired projection images by employing certain image processing techniques such as segmentation, filtration, thrersholding, edge detection and so forth. The segmentation of markers may be performed using suitable operators from image processing, e.g., matched filters, edge detectors, Hough transform for clustering of points into certain structures, etc. For high-accuracy results, these processing techniques may be specifically optimized for sub-pixel accuracy. Also, some characteristics of the phantom support structure may be leveraged to optimize the pre-processing. In one example, the support structure consists of an acrylic cylinder, and the preferred orientation of edges in the image due to that cylinder may be utilized to further optimize the pre-processing. If the markers are arranged in a specific pattern (e.g., along a line, or along a smooth curve), this arrangement and the resulting correlation between markers shadows locations can be leveraged to further improve accuracy in the detected marker shadow locations. Solving the correspondence problem can also be addressed using different methods, e.g., using empirical approaches, information about different marker sizes, etc. Some aspects of the phantom design (e.g., marker sizes) may be chosen such as to facilitate a better solution for the correspondence problem. One step in the correspondence problem may consist of clustering different detected markers into strings of markers, and one option to solve this problem consist of using the Hough transform. As will be appreciated by one skilled in the art, other approaches from image processing may also be used, as appropriate.

While identifying marker shadows in the projection images, the location of the shadows has to be determined with high accuracy, and in some embodiments the correspondence problem needs to be solved, both of which may be done manually. For an automatic solution to these problems, spherical markers, or markers that are defined relative to straight lines (e.g., rods, straight wires, or edges of plates or polygons), may be employed. In each case, the location of the markers may generally be determined with sub pixel accuracy. To solve the correspondence problem, different methods may be employed that help to uniquely identify each marker, e.g., by size, or by using a somewhat constrained geometrical arrangement (e.g., the markers may be arranged in a monotonically increasing fashion in one direction), or the markers may be linked sequentially in some identifiable fashion (for example, BBs that are located along a wire, thus by tracking the wire the sequence of markers can be identified). The calibration phantom may also consist, for example, of straight wires (or rods) that are arranged suitably along the edges of a polygon. In this example, the vertices of the polygon may be used as markers. Additionally, it should be noted that the markers may not be defined as separate points. For example, big spherical markers may also be used, and conclusions about magnification etc. may be drawn from the contours of the shadows, and the estimate of the 3D location of the markers may involve estimating location and size of the spheres. Similarly, for example flat plates with straight edges may be used. Different combinations of these phantom elements may also be used for the calibration techniques mentioned above and other known calibration techniques.

In a framework where the initial estimate of the relative projection geometry between views is reasonably accurate, the correspondence problem may also be solved by using the minimum distance between backprojected markers as the correspondence criterion. For example, shadows of a marker in two views are determined to correspond to the same marker if the line joining the shadow of the marker in one view to the associated focal spot position is closer to the line joining the shadow of that marker in another view with the associated focal spot, than to any other such line. That is, pairs of such lines, that are closest to each other, determine the correspondence. Other techniques may also be built on that approach, using e.g., more than just two views, maybe in combination with a type of cluster analysis, which determines the markers to correspond to clusters of lines that are close together. In another embodiment, a volumetric 3D image may be reconstructed based on an initial estimate of the imaging geometry, and the marker locations may be identified within the reconstructed volume.

The present technique also describes certain phantom designs to be used with the calibration methods described above and other alternative methods. For example, in certain embodiments, a helical phantom may be used. For increased calibration accuracy, the length and the diameter of the helix should be relatively large, which in turn leads to potential superimposition of marker shadows in the projection images, thereby complicating the correspondence problem. Embodiments of the present technique include variations of a helix configuration. For example: (i) a helix arrangement, where the slope of the helix (i.e., ratio of angular displacement of the helical curve to the longitudinal displacement) is smallest at the center of the phantom, and increases towards the ends of the phantom; and/or (ii) a helical arrangement, where the radius of the helix is largest at the center of the phantom, and decreases towards the ends of the phantom; may be used to increase the calibration accuracy and/or to solve the correspondence problem.

As will be appreciated by one skilled in the art, in the embodiments discussed above, the markers are configured so as not to overlap when scanned over a range of view angles by the volumetric imaging system. The markers are configured on the supporting structure so as to permit separate identification of each marker in a collection of projection images. In certain embodiments one or more identifiable marker (such as a sphere that is larger in size than other spheres) may be placed in the set of markers of the phantom. Further, these discrete and opaque markers are spaced apart from one another and embedded on or within a radiographically transparent or partially transparent supporting structure such as a cylinder or a polyhedron that may be made of solid plastic or other radiographically transparent or partially transparent material. It should be noted that transparent, partially transparent and opaque is being referred with respect to the radiation emitted from the radiation source of the volumetric imaging system.

An improved calibration accuracy (over the helix phantoms) may further be achieved by using e.g., a 'candy cane' phantom 80, 82, where multiple helical or elongated patterns are intertwined with each other, as illustrated in FIG. 6 and FIG. 7. More generally, the phantoms as illustrated consist of several copies of basic elongated patterns of markers that are repeated with a rotational offset. In the 'candy cane' phantom 80 illustrated in FIG. 6, the pattern of markers 86 is a 'helical string' 84 that performs a 90 degree rotation along the length of the phantom, and this 'helical string' pattern 84 is repeated four times, with a rotational offset of 90 degrees between the different copies. In the 'candy cane' phantom 82 containing rods 88, as illustrated in FIG. 7, an elongated pattern 90 consisting of three rods 88 is repeated four times, again with an offset of 90 degrees. As will be appreciated by one skilled in the art, other patterns of markers, numbers of elongated patterns, and rotational offsets between elongated patterns of markers are also possible. The phantom may have a cylindrical shape, or a polygonal cross-section. For an easy solution of the correspondence problem, some markers may have a bigger size; or some markers may have a different shape. The projection images 92 and 94 of the respective 'candy cane' phantoms 80 and 82 are also illustrated in FIG. 6 and FIG. 7.

The advantages of the phantom design described above are the following: (i) Easy correspondence problem in spite of superimposition of markers; (ii) Easy estimation of initial geometry. Based on 'turning direction of the screw' formed by the intertwined "strings" it is easy to identify, for example, a subset of markers that are relatively close to the tube; (iii) Increased accuracy in preprocessing using linear assumption on rod edges, or "smoothness assumption" on relative marker placements (along a smooth curve in 3D), both laterally and longitudinally. Other, less regular/symmetric phantom designs may also be used, based on the described concepts. These concepts may also be augmented with other structures such as plates or polygons with accurately known dimensions, or other structures with accurately known dimensions. It should be noted that a phantom may contain a subset of markers that are very accurately placed, or some plates (or similar structures) with highly accurate dimensions. The accuracy cost is on single sub-element, not on full phantom.

As described earlier with reference to FIG. 4 there are 9 different error vectors/geometry parameters, and in one embodiment each marker contributes 2 equations to the error decomposition. Therefore, generally at least 5 markers are required. In specific situations, where some parameters of the geometry may be constrained, fewer parameters need to be estimated, i.e., a correspondingly smaller number of markers may be employed. For example, in one embodiment, in some tomosynthesis systems, a fixed height of the focal spot above the detector may be assumed. Further, as discussed above, the error for each marker may be defined differently, and a marker may have more than a single "reference point", thus any marker may define more than two, or maybe also just one, error equation. Therefore, the minimum number of markers that is required for a complete calibration may vary, as a function of these considerations. However, to manage noise (e.g., due to errors when estimating the location of marker shadows), using a number of markers that is higher than the absolute minimum required may be beneficial. A higher number of markers may also help in managing the concurrent estimation of the 3D marker configuration, if it is not known. In some cases, in particular when a relatively large number of markers is used, not all markers need to be identifiable in all images in order to successfully estimate the imaging geometry.

The above derivation of the decomposition of the error into components that are associated with different specific parameters of the imaging geometry relied on the fact that the object has different "layers", i.e., for any given projection the markers need to be arranged in a range of distances relative to the focal spot. It should be noted that this constraint is only required if the corresponding parameters of the imaging geometry may indeed assume different values. Further, it should be noted that anatomical landmarks, or implants etc., may also be used as markers, provided their spatial relationship is suitable. These anatomical landmarks may also be used in conjunction with additional markers. Also, the calibration markers may be present in the field of view while imaging a patient/anatomy. In this way the patient images may be also used for calibration prior to reconstruction. The system calibration may also be performed separately, where one relies on the repeatability of the system when reconstructing 3D datasets from subsequently acquired patient datasets.

As will be appreciated by one skilled in the art, the phantom may not be made of a rigid structure. For example, in certain embodiments, the phantom may be collapsible and hence may be easy to use. Such phantoms are made of collapsible supporting structure and may include a 'hoberman sphere' or other similar arrangements, or they may use folding patterns from packaging (e.g., boxes, etc.) or other applications. The support structure for the markers may be transparent to the radiation, and markers may be mounted on or within the support structure depending on the phantom design. The collapsible phantom may include some highly accurate components such as polygonal or circular plates. Alternatively, distances between subsets of markers may be highly accurate for the collapsible phantom.

It should be noted that the phantom geometry (or the geometry of subsets of markers) may be estimated beforehand, using a separate calibration run (on an imaging system with a highly accurate geometry). Alternatively, in certain embodiments, the specific position (both absolute and relative) of the reference points (markers) is not accurately specified before a geometry calibration is performed, i.e., using the approach both the accurate 3D position of the markers and the 3D imaging geometry may be estimated simultaneously.

As will be appreciated by one skilled in the art, the calibration techniques and a family of calibration phantom design described in various embodiments discussed above provides determination of geometric parameters of the volumetric imaging system with greater accuracy thereby enabling better calibration of the imaging system for generating better images. In fact, the calibration approaches in various embodiments discussed above do not even require a very specific or highly accurate phantom geometry. Further, as will be appreciated by one skilled in the art, the calibration techniques described above may be used with any conventional phantom design known in the art. Similarly, the phantom designs described above may be used with many other calibration approaches known in the art.

The various embodiments discussed above comprises calibration techniques for analyzing the system geometry of a 3D imaging system using reference points or structures that are visible/detectable in the acquired projection images. This approach may be used, for example, for geometry calibration, or for marker-based 2D to 3D registration. Further, the calibration techniques may also be used in development of enhanced 3D imaging capabilities on surgical C-arm systems, and may also be employed for other systems, including cardiovascular systems and tomosynthesis systems.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for geometrical calibration of a volumetric imaging system, the method comprising:
   computing a projection error between estimated locations of a set of markers of a phantom based on an estimated imaging geometry and observed locations of the respective markers for at least one projection image;
   decomposing the computed projection error into two or more different, specific error components corresponding to respective parameters of the estimated imaging geometry, wherein the two or more different, specific error components are independent of each other; and updating at least one parameter of the estimated imaging geometry based on at least one of the two or more error components.

2. The method of claim 1, further comprising iterating the steps of computing a projection error, decomposing the computed projection error and updating the at least one parameter of the estimated imaging geometry.

3. The method of claim 2, further comprising selectively updating one or more parameters in each iteration.

4. The method of claim 2, further comprising computing projection error consisting of different error terms and decomposing the computed projection error in each iteration.

5. The method of claim 1, further comprising establishing an initially estimated imaging geometry.

6. The method of claim 1, further comprising acquiring one or more projection images of the phantom.

7. The method of claim 1, further comprising identifying the observed locations of the markers in each of the one or more acquired projection images.

8. The method of claim 7, further comprising establishing a correspondence between the markers in each of the one or more acquired projection images and the markers in the phantom.

9. The method of claim 8, wherein establishing the correspondence comprises reconstructing three-dimensional model of the marker locations in the phantom based on the estimated imaging geometry from the plurality of acquired projection images and establishing the correspondence between the phantom and the reconstructed phantom model.

10. The method of claim 9, wherein reconstructing comprises backprojecting the identified locations of the markers and estimating three-dimensional positions of the markers from the backprojected data.

11. The method of claim 1, further comprising reconstructing three-dimensional model of the phantom based on the estimated imaging geometry from the plurality of acquired projection images.

12. The method of claim 11, further comprising establishing a correspondence between the phantom and the reconstructed phantom model.

13. The method of claim 11, further comprising identifying the markers in the reconstructed phantom model.

14. The method of claim 1, further comprising estimating locations of the markers in each of the one or more acquired projection images based on the estimated imaging geometry.

15. The method of claim 1, wherein the projection image of the markers is acquired along with a projection image of an imaged anatomy, and wherein the estimated imaging geometry is established relative to a previously acquired volumetric image of the respective anatomy.

16. The method of claim 1, wherein said decomposing comprises at least one of: decomposing based on Taylor-like expansion around said estimated imaging geometry and image based decomposing.

17. A method for geometrical calibration of a volumetric imaging system, the method comprising:
acquiring a plurality of projection images of a phantom, the phantom comprising a set of markers;
identifying true locations of the markers in each of the plurality of projection images;
establishing an initial estimate of the imaging geometry;
establishing estimated locations of the markers;
computing a projection error between the estimated locations of the markers and the true locations of the respective markers for at least one projection image;
decomposing the computed projection error into two or more different, specific error components corresponding to respective parameters of the estimated imaging geometry, wherein the two or more different, specific error components are independent of each other; and
updating at least one parameter of the estimated imaging geometry based on at least one of the two or more error components.

18. The method of claim 17, further comprising iterating the steps of establishing estimated locations of the markers, projecting estimated locations of the markers, computing a projection error, decomposing the computed projection error and updating the at least one parameter of the estimated imaging geometry.

19. The method of claim 17, further comprising establishing a correspondence between the markers in each of the one or more projection images and the markers in the phantom.

20. The method of claim 17, wherein establishing estimated locations of the markers comprises reconstructing three-dimensional model of the phantom based on the estimated imaging geometry from the plurality of projection images.

21. The method of claim 20, wherein reconstructing comprises backprojecting the identified locations of the markers and estimating three-dimensional positions of the markers from the backprojected data.

22. The method of claim 17, wherein said decomposing comprises at least one of: decomposing based on Taylor-like expansion around said estimated imaging geometry and image based decomposing.

* * * * *